United States Patent [19]

Schratt et al.

[11] 4,445,790

[45] May 1, 1984

[54] APPARATUS FOR CRYOGENIC PROOF TESTING OF ROTATING PARTS

[75] Inventors: John F. Schratt, Riviera Beach; Joseph J. Weber, West Palm Beach, both of Fla.

[73] Assignee: United Technologies Corporation, Hartford, Conn.

[21] Appl. No.: 366,115

[22] Filed: Apr. 7, 1982

[51] Int. Cl.³ ............................................. G01N 25/00
[52] U.S. Cl. ......................................... 374/45; 374/47; 62/64
[58] Field of Search ..................... 374/45, 46, 47, 50; 62/514 R, 373, 64, 55.5, 62; 148/125, 4

[56] References Cited

U.S. PATENT DOCUMENTS

| | | | |
|---|---|---|---|
| 3,442,091 | 5/1969 | Klipping et al. | 62/514 R |
| 3,646,775 | 3/1972 | Bonnerot | 62/514 R |
| 3,909,225 | 9/1975 | Rooney | 62/514 R |
| 4,388,814 | 6/1983 | Schilling | 62/514 R |

FOREIGN PATENT DOCUMENTS

| | | | |
|---|---|---|---|
| 526289 | 12/1929 | Fed. Rep. of Germany | 62/514 R |
| 227658 | 1/1969 | U.S.S.R. | 374/45 |
| 535556 | 11/1976 | U.S.S.R. | 374/47 |
| 728039 | 4/1980 | U.S.S.R. | 374/45 |

Primary Examiner—Charles Frankfort
Assistant Examiner—David R. Schuster
Attorney, Agent, or Firm—Jack N. McCarthy

[57] ABSTRACT

An apparatus to test a rotating metal part at a cryogenic temperature is disclosed. This apparatus includes an inner chamber wherein a metal part can be mounted for rotation and brought to a cryogenic temperature and then placed in a vacuum. The container wall is formed to contain a cryogenic liquid and a cover is placed over the container which also includes a cryogenic liquid. Insulating material is used around the container and control valves and conduits provide for fluid transfer within the apparatus.

7 Claims, 2 Drawing Figures

APPARATUS FOR CRYOGENIC PROOF TESTING OF ROTATING PARTS

The Government has rights in this invention pursuant to Contract No. F33657-79-C-0002 awarded by the Department of the Air Force.

CROSS REFERENCE

This invention is related to the invention disclosed in co-pending application Ser. No. 366,114, now U.S. Pat. No. 4,427,304 entitled METHOD OF CRYOGENIC PROOF TESTING OF ROTATING PARTS, filed by Frank C. Gillette, Douglas H. Nethaway and Ernest C. Bryan on even date and assigned to the same assignee of this application.

TECHNICAL FIELD

This invention relates to apparatus for cryogenic proof testing of rotating parts and particularly to rotating parts such as engine discs and blades of aircraft. As is well known in the gas turbine engine art, the durability of engine components is of paramount importance, and obviously, the longer an engine component endures, the longer an engine can perform without the costly removal of an engine necessitated by the repair or replacement of such components. Presently, for example, the maintenance plan for engine discs requires retirement of a part much sooner than necessary. Current inspection procedures are fluorescent penetrant, eddy current and sonic non-destructive tests which may typically provide for an expectant life of 1400 hours; whereas, cryogenic proof test will allow part usage to 2400 hours. In addition, current inspection methods are susceptible to human error due to the nature of these inspection methods; whereas, this cryogenic proof test is essentially foolproof since it is dependent upon the material characteristics, part configuration, and the magnitude of loading during the test.

BACKGROUND ART

U.S. Pat. Nos. 3,250,901 and 4,046,002 show systems for indicating the service operational life of an engine part such as a rotor, U.S. Pat. Nos. 3,273,636 and 3,465,569 set forth two types of chambers which include the use of a cryogenic fluid to control the temperature therein.

DISCLOSURE OF INVENTION

It is an object of this invention to provide an apparatus to test a rotating metal part at a cryogenic temperature.

Another object of this invention is to provide an apparatus having a container with an inner fluid container wall wherein a metal part can be mounted for rotation, cooled to a cryogenic temperature, placed in a vacuum, and then rotated to place said part under a desired stress.

A further object of this invention is to provide an apparatus having a container with an inner container wall and means for mounting a metal part therein for rotation, means for filling said inner fluid container wall with a cryogenic liquid to immerse said metal part, means for draining said cryogenic liquid from said inner container wall and placing a vacuum within said wall, means for rotating said part and placing a desired stress thereon.

Another object of this invention is to provide a cover for said inner fluid container wall having an inner chamber for containing liquid nitrogen and an outer chamber having a vacuum placed therein.

BEST MODE FOR CARRYING OUT THE INVENTION

Figure 1:
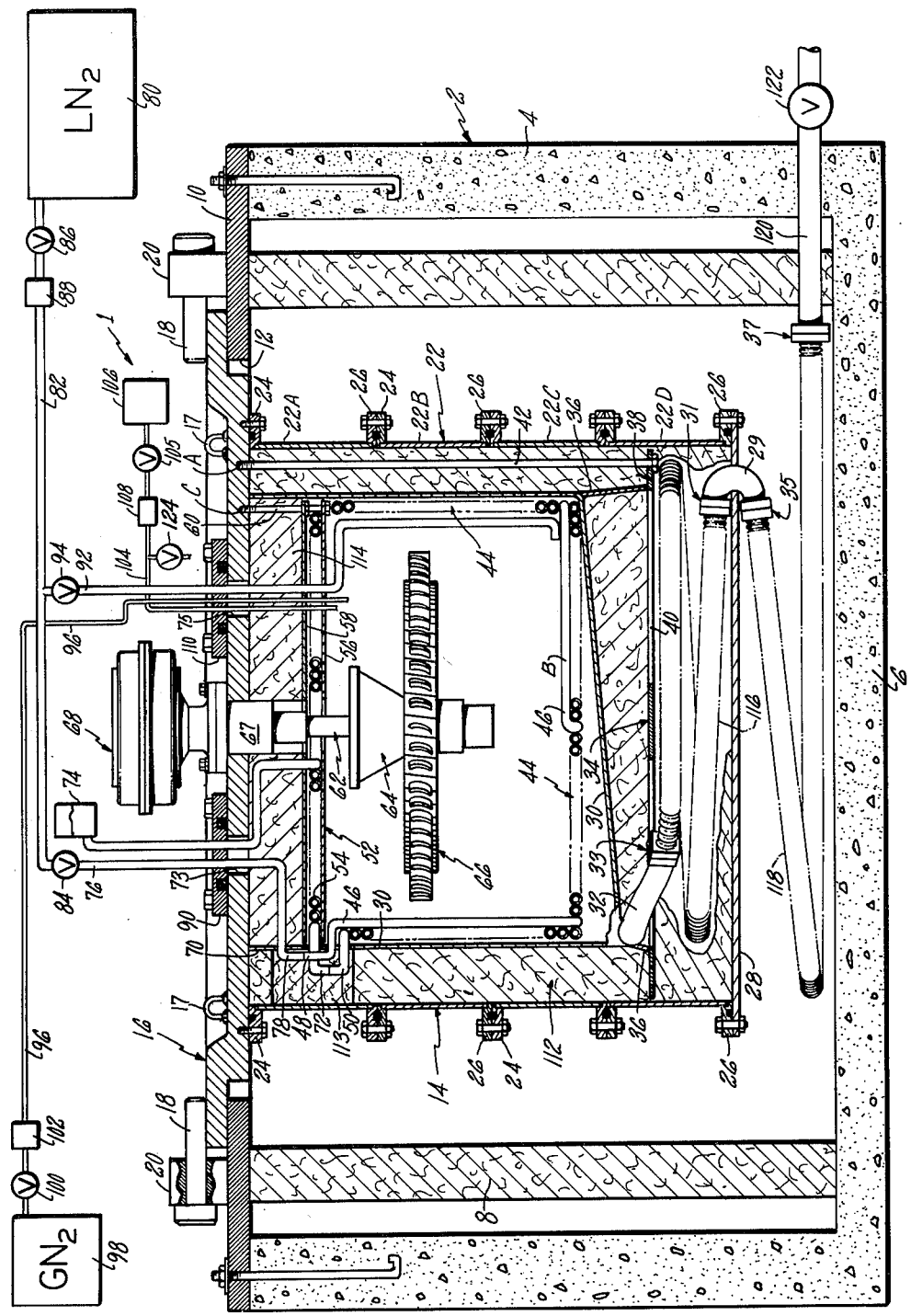
FIG. 1 is a sectional view of a test spin pit containing a cryogenic spin testing chamber with means for obtaining a proper cryogenic temperature therein, shown schematically.

As seen in FIG. 1, a test spin apparatus 1 is shown wherein rotatable parts can be rotated in a cryogenic atmosphere and the part contained if it is subjected to a bursting condition. The outer container structure is a spin pit 2 formed of a continuous reinforced concrete and steel containment wall 4 and a bottom pad 6. A wall 8 of energy absorption material is located around the interior of the wall 4. The container structure has a steel top 10 with an outer edge secured to the top of the containment structure 2. The top 10 has an opening 12 at the center thereof for the insertion and removal of a cover 16 and cryogenic spin testing chamber 14.

The cover 16 is sized to fit into the opening 12 and overlap the steel top 10 around the periphery of the opening 12. Lock pins 18 are slidably mounted in bosses 20 placed around the steel top 10. These slidably mounted pins can be placed between an inward position, as shown in FIG. 1, where they lock the cover 16 in place on the top 10, and in a withdrawn position (not shown) where the cover 16 can be removed along with any attachments thereto, as will be hereinafter described.

The cryogenic spin testing chamber 14 consists of a vacuum can 22 forming the outer surface, said vacuum can comprising four individual sections—22A; 22B; 22C; and 22D; each section having a peripheral flange 24 at the top thereof and a peripheral flange 26 at the bottom thereof. When assembled, the top peripheral flange 24 of section 22A is bolted to the bottom of the cover 16; the bottom peripheral flange 26 of section 22A is bolted to the top of peripheral flange 24 of section 22B. The successive sections are fixed together in the same manner until the last section 22D is reached and the bottom peripheral flange 26 of this section is bolted to a bottom plate 28 which has a short drain pipe 29 fixed thereto extending from the interior to the exterior of the vacuum can 22. An O-ring is placed between each mating surface of peripheral flange 24 and 26 inwardly of the bolt locations around the flanges; an O-ring is placed between the top peripheral flange 24 of section 22A and the internal side of cover 16, and the bottom peripheral flange 26 of section 22D and the internal side of bottom plate 28 in a like manner (see FIG. 1).

A cryogenic fluid containing tank 30 is positioned within the vacuum can 22 for containing a cryogenic liquid to obtain a desired cryogenic temperature around a part to be tested. The cryogenic fluid containing tank 30 is formed of a metal compatible with the liquid to be used therein (an AISI 300 Series stainless steel tank was used in an installation) and has an open top and a bottom which is tapered to direct fluid into a drain pipe member 32. A supporting plate 34 is fixed to the bottom of the cryogenic fluid containing tank 30 by a plurality of metal supports 36. The supporting plate 34 is formed having a peripheral plate section 38 with a center X-shaped portion 40. This provides a spacing for the drain pipe member 32 to extend therethrough for a purpose to be hereinafter described. If desired, the plate 34 could be solid with merely one opening for the drain pipe member 32. A plurality of long holding bolts 42 are spaced around the peripheral portion of the plate 34 and are bolted into the underside of the cover 16 at points A. These bolts are tightened to carry the weight of tank 30, connected parts, to be hereinafter described, and fluid therein.

The cryogenic fluid containing tank 30 contains an inner liner 44 formed for approximately three-fourths of its height of tubular construction. A tube 46 having an inlet 48 enters the cryogenic fluid containing tank 30 at a point downwardly from the top of the tank 30 and extends to a point adjacent the bottom of the tank 30 where it is then coiled inwardly toward the center providing a flat tubed wall across the bottom. The tube 46 then is carried radially at B to a point adjacent the side of the tank 30 and then coiled around the interior of the side of the tank upwardly to a point marking approximately three-fourths of the height of the tank 30 where it then extends through the side of the tank to the exterior thereof to an outlet 50. The attachment of the inlet 48 and outlet 50 will be hereinafter discussed.

Cover 16 has a tank insert 52 extending downwardly therefrom which fits into the upper approximately one-fourth remaining open portion of the cryogenic fluid containing tank 30. Tank insert 52 is formed at its lower end by a tubular flat coil 54 which is positioned between two plates 56 and 58. The two spaced plates are bolted to the underside of the cover 16 by a plurality of bolts 60 at points C. Each bolt 60 has its head supporting the plate 56 and an intermediate nut, or stop member, supporting the plate 58. The plates 56 and 58 have a central opening to accommodate the extension of a rotating shaft means 62. This shaft means 62 is connected to a spin arbor 64 which is adapted to hold a test disc 66.

The rotating shaft means 62 extends through a lateral displacement vibration damper 67 having a vacuum seal contacting rotating shaft means 62. The damper 67 is fixedly positioned in an opening in cover 16 which is aligned with the central openings in plates 56 and 58. A drive means 68 is drivingly connected to rotating shaft means 62 to provide for the rotation thereof while the housing for the drive means 68 is fixedly mounted to the top of cover 16. Seal means, such as an "O" ring, (not shown) are provided between the fixed mounting structure of the drive means 68 and the cover 16. Drive means 68 can be an air turbine or electric motor. The outer end of the tubular flat coil 54 extends through the bottom of a longitudinal slot 70 in the upper end of the cryogenic fluid containing tank 30 to the exterior thereof to an inlet 72; and the inner end of the tubular flat coil 54 extends upwardly through plate 58 adjacent its central opening and extends through an opening 73 in cover 16 to pressure vent and cryogenic fluid level indicator 74. A tubular member 76 extends through the same opening 73 in cover 16 and extends through the upper part of slot 70 to the exterior of the cryogenic fluid containing tank 30 to an outlet 78. Liquid nitrogen tank 80 has a conduit 82 connected to tubular member 76 by shut-off valve 84. An on-off valve 86 is located in line 82 adjacent the liquid supply tank 80. A connect-disconnect means 88 is located between valve 86 and valves 84 and 94.

A seal plate 90 is mounted to the top of cover 16 to form a vacuum seal around the opening 73. An O-ring seal extends around the opening 73 and fits in an annular groove in the mating surface of seal plate 90. The seal plate 90 is held on by bolts. The inner end of tubular flat coil 54 and tubular member 76, extending through opening 73, are fixedly mounted in the seal plate 90, such as by welding or bonding. Outlet 78 of tubular member 76 is connected to inlet 48 of tube 46, such as by soldering, to carry liquid nitrogen from tubular member 76 into tube 46, and the inlet 72 of the tubular flat coil 54 is connected, such as by soldering, to the outlet 50 of the tube 46 to carry liquid nitrogen from tubular member 46 into tubular flat coil 54. While these connections are shown as solder joints, other tube connecting means can be used.

A second opening 75 is located in cover 16 for connecting operating conduits between the upper side of cover 16 and the interior of the cryogenic fluid containing tank 30 within vacuum can 22. A conduit 92 extends through the opening 75 where its external end is connected to conduit 82 between valve 84 and disconnect means 88. The interior portion of conduit 92 extends through plates 56 and 58 and follows the inner tubular liner of the tank 30 to a point adjacent the bottom thereof. A valve 94 is located in conduit 92 adjacent its connection to conduit 82. A second conduit 96 extends through opening 75 and through plates 58 and 56 into the top of tank 30, while above the cover 16, the conduit 96 is connected to a gaseous nitrogen supply tank 98. A valve 100 is located in conduit 96 adjacent the gaseous nitrogen supply tank 98 and a connect-disconnect means 102 is located between valve 100 and cover 16. A third conduit 104 extends through opening 75 and through plates 58 and 56 into the top of tank 30; while above the cover 16, the conduit 104 is connected to a vacuum pumping device 106. A connect-disconnect means 108 is located in conduit 104 and a valve 105 is located between vacuum pump 106 and connect-disconnect means 108. Check valve means 124 are provided in conduit 104 for venting tank 30 when necessary. A second seal plate 110 is mounted to the top of cover 16 to form a vacuum seal around the opening 75. An O-ring seal extends around the opening 75 and fits into an annular groove on the mating surface of seal plate 110. The seal plate 110, similar to seal plate 90, is held on by bolts. Any other well known holding means can be used. The conduits 92, 96 and 104, extending through opening 75, are fixedly mounted in the seal plate 110, such as by welding or bonding.

Insulating means 112 are provided between the vacuum can 22 and the cryogenic fluid containing tank 30 to maintain desired cryogenic temperatures within the tank 30; and insulating means 114 are provided on the top of plate 58. Said insulating means 114 is fixedly held against the inside of cover 16 by plate 58. The insulating means 112 and 114 can be made up of many types of insulating material known in the prior art. The portion of the insulating means 112 above plate 34 can be of a substantially solid type fixed to move with the cryogenic fluid containing tank 30 as it is moved with relation to vacuum can 22. One part 113 of the insulating means 112 located over and around the inlet 48 and outlet 50 of tube 46, inlet 72 of tubular flat coil 54, and outlet 78 of conduit 76, is made to be easily removable to gain access to these inlets and outlets so that they can be conveniently connected and disconnected. The portion of the insulating means below plate 34 can be of a type contoured to fits around a flexible convoluted metal hose 116 connecting the drain pipe member 32 to the interior end of drain pipe 29. The convoluted metal hose 116 has a connect-disconnect means 33 at one end connecting it with drain pipe member 32 and a connect-disconnect means 31 at the other end connecting it with the inner end of drain pipe 29. The exterior end of drain pipe 29 is also connected by a flexible convoluted metal hose 118 to a drain line 120 extending through the energy absorbing wall 8 and the reinforced concrete wall 4. The convoluted metal hose 118 has a connect-disconnect means 35 at one end connecting it with the outer end of drain pipe 29 and a connect-disconnect means 37 at the other end connecting it with the end of drain line 120 within energy absorbing wall 8. A valve 122, located in drain 120, controls drain flow from the cryogenic fluid containing tank 30.

OPERATION

With the apparatus as shown in FIG. 1, it can be used to provide cryogenic proof testing of a rotating part as follows: With all the valves closed;

(1) place vacuum can 22 under a vacuum of 0.3 to 0.5 mm mercury by opening valve 105. Close valve 105 and open valve 100 to fill vacuum can 22 with gaseous dry nitrogen (GN$_2$) to atmospheric pressure. Repeat this two-step sequence as necessary to remove moisture from cryogenic spin testing chamber 14;

(2) with valve 105 closed, open valves 86 and 94 and fill the cryogenic fluid containing tank 30 with liquid nitrogen (LN$_2$) to predetermined level above test disc 66 (venting takes place automatically with check valve 124 opening as necessary);

(3) close valve 94 and open valve 84 and fill tube 46 and tubular flat coil 54 to desired level as indicated by cryogenic fluid level indicator 74, with liquid nitrogen (LN$_2$), close valve 84;

(4) soak disc for a time sufficient to achieve a stabilized cryogenic temperature throughout the test disc 66, maintaining a predetermined liquid nitrogen level above test disc 66 (determined by observing the liquid nitrogen (LN$_2$) level through porthole in cover 16, not shown) by opening valves 86 and 94 as needed;

(5) with valve 94 closed, open valve 122 and drain liquid nitrogen (LN$_2$) from cryogenic fluid containing tank 30; when liquid nitrogen (LN$_2$) level is below the disc, spin disc at approximately 300 to 400 rpm for a few seconds to force residual liquid nitrogen (LN$_2$) off the test disc 66;

(6) after completion of drain, close valve 122 and open valve 105 and place vacuum can 22 under vacuum of 1 mm mercury or better;

(7) spin disc 66 to a predetermined test speed; (hold for predetermined time period if desired).

After the cryogenic proof testing of a rotating part has been completed, the apparatus 1 can be torn down in the following manner to remove the test disc and replace it by the next part to be tested:

(1) close valve 105 and open valve 100, filling vacuum can 22 with gaseous dry nitrogen (GN$_2$) to atmospheric pressure (valve 124 venting) and flow gaseous nitrogen (GN$_2$) until the interior of tank 30 reads warmer than 32° F. (0° C.); using heated gaseous nitrogen (GN$_2$) optional;

(2) move lock pins 18 to their unlocked position;

(3) disconnect conduits 82, 96 and 104;

(4) lift chamber 14 out of the spin pit 2 by hooking onto lifting eyes 17 on cover 16;

(5) when the connect-disconnect means 35 can be reached, disconnect the drain pipe 29 from the convoluted metal hose 118;

(6) completely remove chamber 14 out of the spin pit 2;

(7) unbolt top peripheral flange 24 of section 22A from cover 16;

(8) separate unbolted cover 16 and flange 24, removing tank 30 and connected parts from the vacuum can 22;

(9) when the connect-disconnect means 33 can be reached, disconnect the drain pipe member 32 from the convoluted metal hose 116;

(10) completely remove tank 30 and connected parts out of the vacuum can 22;

(11) remove insulating parts 113 from around inlet 48, outlet 50, inlet 72, and outlet 78 so that inlet 48 can be disconnected from outlet 78 and outlet 50 can be disconnected from inlet 72;

(12) disconnect inlet 48 from outlet 78 and outlet 50 from inlet 72; as shown, this is done by de-soldering;

(13) unbolt plate 34 from cover 16;

(14) separate tank 30 from cover 16 and tank insert 52; exposing the spin arbor 64 and test disc 66;

(15) remove test disc 66 and spin arbor 64 from shaft 62.

Reverse order of teardown for subsequent test setup.

Figure 2:
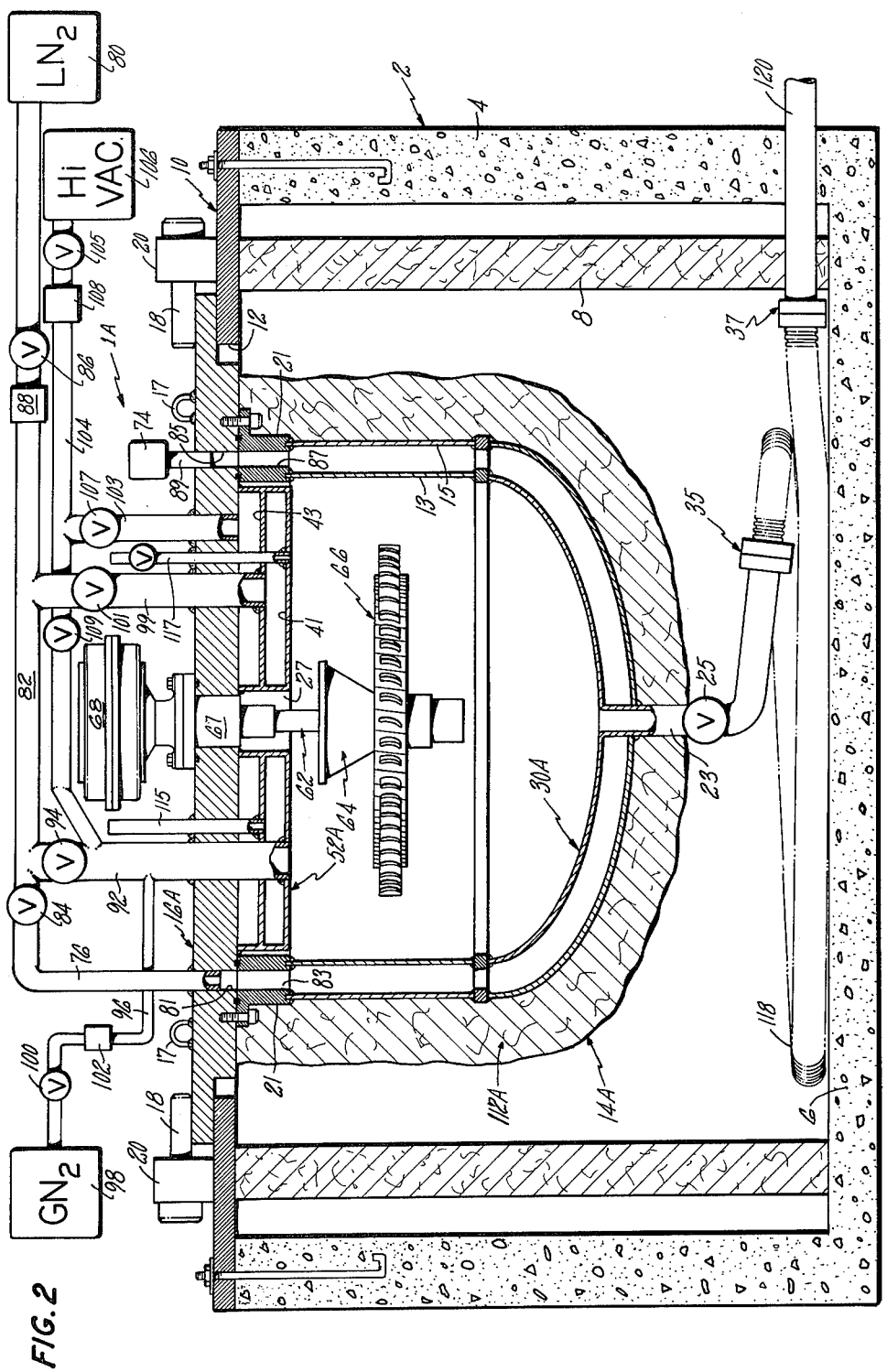
FIG. 2 shows another modification of the cryogenic spin testing chamber.

As seen in FIG. 2, a modification of a test spin apparatus 1A is shown. The outer container structure includes a similar spin pit 2 and reinforced concrete and steel containment wall 4 and bottom pad 6. A wall 8 also absorbs energy within the wall 4. The steel top 10 is the same and has its outer edge secured to the top of the containment structure 2. A cover 16A is positioned on the top 10 in a manner similar to that of FIG. 1, including the lock pins 18 in bosses 20 fixed to the steel top 10.

The cryogenic spin testing chamber 44A consists of a double walled container 30A having an inner wall 13 and an outer wall 15. The open ends of the double walls are fixed to an annular ring 21 which is bolted to the bottom of the cover 16A. O-rings are placed between the mating surface of the annular ring 21 and the undersurface of the cover 16A to provide for sealing therebetween. Insulating material 112A is placed around the outer wall 15 of the double walled container 30A. A drain pipe 23 extends from inner wall 13 through outer wall 15 to a point below the insulating material 112A. A remotely operated valve 25 is located in said drain pipe 23. Pipe 23 is sealed with outer wall 15.

Cover 16A has a container insert 52A extending downwardly therefrom which fits into the inner opening of annular ring 21. Container insert 52A is formed having a central opening 27. The container insert 52A is also formed having two annular chambers 41 and 43. Opening 27 accommodates the extension of a rotating shaft means 62. This shaft means 62, as shown in FIG. 1, is connected to a spin arbor 64 which is adapted to hold a test disc 66.

The rotating shaft means 62 extends through a lateral displacement vibration damper 67 having a vacuum seal contacting rotating shaft means 62. Damper 67 is fixedly positioned in an opening in cover 16A, which is aligned with opening 27 in container insert 52A. A drive means 68 (such as an air turbine or electric motor) is drivingly connected to rotating shaft means 62, as shown in FIG.

1, to provide for the rotation. The drive means 68 is vacuum sealed to the cover 16A.

A liquid nitrogen tank 80 has a conduit 82 connected to a conduit section 76 by valve 84; connected to a conduit section 92 by valve 94; and connected to a conduit section 99 by valve 101. The direct liquid nitrogen between the inner wall 13 and outer wall 15, conduit section 76 is connected by a passageway 81 in cover 16A and aligned passageway 83 in annular ring 21 to connect it to the interior of the space between inner wall 13 and outer wall 15. The space between the outer wall 15 and inner wall 13 is connected by a passageway 87 in annular ring 21, passageway 85 in cover 16A, and conduit 89 to a pressure vent and cryogenic fluid level indicator 74. To direct liquid nitrogen into the space between walls 13 and 15 of the double walled container 30A, conduit section 92 passes through and is sealed with cover 16A and the two annular chambers 43 and 41 of the container insert 52A. To direct liquid nitrogen into annular chamber 41, conduit section 99 passes through and is sealed with cover 16A and annular chamber 43 of the container insert 52A. An on-off valve 86 is located in line 82 adjacent the liquid supply tank 80 and a connect-disconnect means 88 is located between valve 86 and the connection of conduit section 99.

A gaseous nitrogen supply tank 98 has a conduit 96 connected to conduit section 92 downstream of valve 94. A valve 100 is located in conduit 96 and a connect-disconnect means 102 is located between valve 100 and the connection of conduit 96 to conduit section 92. This permits gaseous nitrogen to be directed inside wall 13 of the double walled container 30A when desired.

A vacuum pumping device 106 has a conduit 104 connected to conduit section 92 downstream of valve 94. A conduit 103 is connected to conduit 104 while its other end passes through and is sealed with cover 16A to be connected to annular chamber 43. A valve 109 is located in conduit 104 between the point where it is connected to conduit 92 and the connection of conduit 103; and a valve 107 is located in conduit 103. A valve 105 is located in conduit 104 adjacent the vacuum pumping device 106; and a connect-disconnect means 108 is located in conduit 104 between valve 105 and the connection of conduit 103 to conduit 104. This permits the interior of wall 13 of double walled container 30A and annular chamber 43 to be placed under a vacuum when desired.

The exterior end of drain pipe 23 is connected by a flexible convoluted metal hose 118 to a drain line 120 extending through the energy absorbing wall 8 and the reinforced concrete wall 4. The convoluted metal hose 118 has a connect-disconnect means 35 at one end connecting it with the outer end of drain pipe 23 and a connect-disconnect means 37 at the other end connecting it with the end of drain line 120 within energy absorbing wall 8. A remotely operated valve 25 controls drain flow from within wall 13 of the cryogenic double walled container 30A. Pressure vents 117 (with associated check valve) and 115, provide venting for filling the interior of container wall 13 and annular chamber 41, respectively.

With the apparatus as shown in FIG. 2, it can be used to provide cryogenic proof testing of a rotating part as follows: With all of the valves closed;

(1) place interior of container wall 13 at a vacuum of 0.3 to 0.5 mm mercury by opening valves 105 and 109. Close valve 109 and open valve 100 to fill this same volume with gaseous dry nitrogen (GN$_2$) to atmospheric pressure. Repeat this two-step sequence as necessary to remove moisture from the interior of the cryogenic spin testing chamber 14A;

(2) place annular chamber 43 under a vacuum of 0.3 to 0.5 mm mercury by opening then closing valves 105 and 107;

(3) with valve 105 closed, open valves 86 and 94 and fill the interior of wall 13 of the double walled container 30A with liquid nitrogen (LN$_2$) to a predetermined level (observing the level through porthole in cover 16A, not shown) above disc 66 (venting automatically through 117 with its check valve);

(4) close valve 94 and open valve 84 and fill the space between inner wall 13 and outer wall 15, to desired level as indicated by cryogenic fluid level indicator 74, with liquid nitrogen (LN$_2$);

(5) close valve 84 and open valve 101 and fill annular chamber 41 with liquid nitrogen (LN$_2$) (venting as necessary through 115); close valve 101;

(6) soak disc 66 for a time sufficient to achieve a stabilized cryogenic temperature throughout the test disc 66, maintaining a predetermined liquid nitrogen level above disc 66 by opening valves 86 and 94 as needed;

(7) with valve 94 closed, open valve 25 and drain liquid nitrogen (LN$_2$) from within wall 13 of container 30A; when liquid nitrogen (LN$_2$) level is below the disc, spin disc at approximately 300–400 rpm for a few seconds to force residual liquid nitrogen (LN$_2$) off the test disc 66;

(8) after completion of drain, close valve 25 and open valves 105 and 109 and place vacuum within wall 13 of container 30A of 1 mm mercury or better;

(9) spin disc 66 to a predetermined test speed (hold for predetermined time period if desired).

After the cryogenic proof testing of a rotating part has been completed, the apparatus 1A can be torn down in the following manner to remove the test disc and replace it by the next part to be tested:

(1) close valve 105 and open valve 100 filling inside of wall 13 of double walled container 30A with gaseous dry nitrogen (GN$_2$) to atmospheric pressure (conduit 117 and associated valve venting) and flow gaseous nitrogen (GN$_2$) until the interior of container 30A reads warmer than 32° F. (0° C.); using heated gaseous nitrogen (GN$_2$) optional;

(2) move lock pins 18 to their unlocked position;

(3) disconnect conduits 82, 96 and 104;

(4) lift chamber 14A out of the spin pit 2 by hooking onto lifting eyes 17 on cover 16A;

(5) when the connect-disconnect means 35 can be reached, disconnect the drain pipe 23 from the convoluted metal hose 118;

(6) completely remove chamber 14A out of spin pit 2;

(7) remove sufficient insulation 112A to unbolt annular ring 21 from cover 16A;

(8) separate unbolted cover 16A and annular ring 21, removing double walled container and connected parts from the cover 16A exposing the spin arbor 64 and test disc 66;

(9) remove test disc 66 and spin arbor 64 from shaft 62.

Reverse order of teardown for subsequent test setup.

We claim:

1. An apparatus for testing a spinning metal part at a desired cryogenic temperature, said apparatus having a container, said container having an inner container wall, cover means for said container, means for mounting a metal part for spinning within said inner container wall, a metal part mounted on said mounting means, means for filling said inner container wall above said metal part with a cryogenic liquid to bring said metal part mounted thereon to a desired cryogenic temperature, means located adjacent said inner container wall to maintain the desired cryogenic temperature within said inner container wall, means for draining said cryogenic liquid from said inner container wall when said metal part has reached the desired cryogenic temperature, means for placing a vacuum in said inner container wall around said metal part when said cryogenic liquid has been drained therefrom, means for spinning said metal part in said vacuum in said inner container wall to place a desired stress on said metal part when it is at the desired cryogenic temperature.

2. An apparatus as set forth in claim 1 wherein said means located adjacent said inner container wall to maintain a cryogenic temperature within said inner container wall comprises an outer container wall spaced therefrom, means for placing a cryogenic liquid in the space between said inner container wall and outer container wall, said cover means including a projection means extending into the top of said inner container wall, said projection means including a chamber adjacent its end in said inner container wall, means for filling said chamber with a cryogenic liquid, said projection means including a second chamber above said first named chamber, means for placing a vacuum in said second chamber.

3. An apparatus as set forth in claim 1 wherein said means located adjacent said inner container wall to maintain a cryogenic temperature within said inner container wall comprises a coiled tube liner around the inside of the inner container wall to a point spaced from the top of said inner container wall and a first flat coiled tube at the bottom of the inner container wall, said cover means including a projection means extending into the top of said inner container wall to a point adjacent the top of said coiled tube liner, said projection means including a second flat coiled tube at its end in said inner container wall, means for filling said first and second flat coiled tube and coiled tube liner with a cryogenic liquid.

4. An apparatus as set forth in claim 1 wherein said means for placing a vacuum in said inner container wall includes an outer container vacuum wall spaced outwardly from said inner container wall, said outer container vacuum wall cooperating with said cover means to permit a vacuum being formed therein.

5. An apparatus as set forth in claim 4 wherein an insulating means is located between said inner container wall and said outer container vacuum wall.

6. An apparatus as set forth in claim 4 wherein said outer container vacuum wall is formed of a plurality of wall sections connected at the top and bottom to each other, the top section being connected to said cover means, a bottom plate being connected to the bottom section.

7. An apparatus as set forth in claim 3 wherein said means for placing a vacuum in said inner container wall includes an outer container vacuum wall spaced outwardly from said inner container wall, said outer container vacuum wall cooperating with said cover means to permit a vacuum being formed therein, said outer container vacuum wall being formed of a plurality of wall sections, each section having a top peripheral flange and a bottom peripheral flange, said wall sections being connected to each other by adjacent top and bottom peripheral flanges, the peripheral flange of the top section being connected to said cover means, a bottom plate being connected to the bottom peripheral flange of the bottom section, insulating material being located between said outer container vacuum wall and said inner container wall.

* * * * *